United States Patent
O

(10) Patent No.: US 7,214,329 B2
(45) Date of Patent: May 8, 2007

(54) STORAGE STABLE AQUEOUS ORGANIC PEROXIDE EMULSIONS

(75) Inventor: Boen H. O, Utrecht (NL)

(73) Assignee: Akzo Nobel N.V., Arnhem (NL)

( * ) Notice: Subject to any disclaimer, the term of this patent is extended or adjusted under 35 U.S.C. 154(b) by 485 days.

(21) Appl. No.: 10/468,907

(22) PCT Filed: Feb. 20, 2002

(86) PCT No.: PCT/EP02/01812

§ 371 (c)(1),
(2), (4) Date: Sep. 11, 2003

(87) PCT Pub. No.: WO02/076936

PCT Pub. Date: Oct. 3, 2002

(65) Prior Publication Data
US 2004/0132938 A1 Jul. 8, 2004

(30) Foreign Application Priority Data
Mar. 23, 2001 (EP) .................................. 01201118

(51) Int. Cl.
C01B 15/10 (2006.01)
C09K 3/00 (2006.01)
C08F 4/34 (2006.01)
C07C 409/00 (2006.01)
C07C 407/00 (2006.01)

(52) U.S. Cl. ........................... 252/186.26; 252/186.42; 252/182.13; 252/182.22; 252/182.29; 526/230

(58) Field of Classification Search ..................... None
See application file for complete search history.

(56) References Cited

U.S. PATENT DOCUMENTS 2,437,420 A * 3/1948 D Alelio ...................... 526/332
2,454,254 A 11/1948 Tonawanda et al.
3,535,422 A * 10/1970 Cox et al. .................... 514/714
3,538,011 A 11/1970 Van Der Klaauw
3,591,567 A * 7/1971 Chihara et al. ........... 526/329.4
4,255,277 A 3/1981 Smearing
4,376,218 A 3/1983 Izzard et al.
5,690,856 A 11/1997 Milleville et al.
6,258,906 B1 * 7/2001 Bodart ........................ 526/227
6,495,623 B1 * 12/2002 Tanimoto et al. ........... 524/459

FOREIGN PATENT DOCUMENTS

| EP | 0 032 757 | 7/1981 |
| EP | 0 343 747 | 11/1989 |
| GB | 1195083 | 6/1970 |
| GB | 1275172 | 5/1972 |
| JP | 79006263 B4 | 3/1979 |
| JP | A 62 086005 | 4/1987 |
| WO | WO 97/27229 | 7/1997 |
| WO | WO 99/05101 | 2/1999 |
| WO | WO 99/05102 | 2/1999 |
| WO | WO 99/31194 | 6/1999 |

OTHER PUBLICATIONS

Wilson, "Plasticisers Principles and Practice," The Institute of Materials, Cambridge University Press, 1996, p. 12, pp. 145-179 (Chapter 5), and pp. 279-280 (Appendix 1).

* cited by examiner

Primary Examiner—Joseph D. Anthony
(74) Attorney, Agent, or Firm—Kenyon & Kenyon LLP

(57) ABSTRACT

The invention relates to an aqueous organic peroxide emulsion comprising an anti-freeze agent, a protective colloid, and a plasticiser wherein the plasticizer is an ester having a ratio of the number of carbon atoms present in the pasticiser molecule (excluding aromatic carbon atoms) to the number of ester groups in the molecule of higher than 8. These emulsions show a reduced droplet growth as compared to emulsions comprising a conventional plasticizer, i.e. the emulsions of the invention are more stable upon storage than the emulsions of the prior art. The invention emulsions are particularly useful in polymerization processes such as the polymerization of vinyl chloride monomer.

9 Claims, No Drawings

STORAGE STABLE AQUEOUS ORGANIC PEROXIDE EMULSIONS

The present invention relates to an aqueous organic peroxide emulsion comprising an anti-freeze agent, a protective colloid, and a plasticiser.

As is well known, organic peroxides are thermally labile compounds. Because the decomposition of these peroxides is exothermic, it is hazardous when the heat of decomposition cannot be dissipated, e.g., by heat loss to the surrounding area. When heat accumulates, the decomposition reaction may run out of control. To avoid such undesired situation, the peroxide typically is formulated with one or more phlegmatising agents including water.

Aqueous organic peroxide emulsions are generally considered safe products because the peroxide is dispersed—forming small droplets—in the water phase, which water phase is well-suited for the removal of the heat of decomposition of peroxide molecules, e.g., by convection and/or evaporation.

However, it was observed that many aqueous organic peroxide emulsions are not sufficiently stable upon storage. Most aqueous organic peroxide emulsions used commercially are stored at low temperatures, typically −25° C. to 0° C. Although emulsion formulations are well optimised with respects to viscosity and droplet size, droplet growth remains a problem, resulting in a short emulsion shelf life time. The growth of droplets may (eventually) result in layer separation of the emulsion, causing a formulation which was thought to be safe to become unsafe. Moreover, in a number of applications, for instance in the manufacture of PVC, the number of fish eyes increases with emulsion age.

JP-A-62086005 relates to an aqueous organic peroxide emulsion comprising a partially saponified polyvinyl acetate with a saponification degree of 5 to 70 mole % as an emulsification stabiliser. By using the partially saponified polyvinyl acetate, layer separation of the emulsion—which is the worst form of emulsion instability—could be prevented. It is described that the stability of the emulsion could be improved further by adding a hydrocarbon-based solvent such as n-hexane, toluene, xylene or IP (iso-paraffin) solvent, a plasticiser such as DBP (dibutyl phthalate), DOP (dioctyl phthalate), and DOA (dioctyl adipate), or a chlorine-based solvent such as methylene chloride, carbon tetrachloride, and tetrachloroethylene. Examples are given using DOP and carbon tetrachloride. A relatively large amount of DOP and carbon tetrachloride (i.e. 10 wt %) appears to have been used in order to obtain the improved emulsion stability.

We found, however, that aqueous organic peroxide emulsions comprising a plasticiser in accordance with the prior art, e.g. DOP, still suffer from instability, i.e. droplet growth upon storage. Accordingly, there is a need for more stable aqueous organic peroxide emulsions, i.e. emulsions which show a reduced droplet growth during storage as compared to those of the state of the art. Preferably, the emulsion stabilising agent should work when used in small amounts.

Incidentally, Applicant's WO 99/31194 discloses aqueous organic peroxide emulsions comprising at least one organic peroxide, water, at least one anti-freeze agent, at least one chlorinated paraffin, optionally at least one non-ionic surface-active agent, and optionally one or more protective colloids. These emulsions have a low viscosity and excellent storage stability for long periods of time. It is mentioned that the organic peroxide may be diluted with a plasticiser such as toluene, aliphatic hydrocarbons or dioctyl phthalate. This document does not disclose or suggest the emulsion in accordance with the present invention.

We found that droplet growth in aqueous organic peroxide emulsions can be reduced by including a specific plasticiser.

The invention is characterised in that the plasticiser is an ester having a ratio of the number of carbon atoms present in the plasticiser molecule (excluding aromatic carbon atoms) to the number of ester groups in the molecule of higher than 8.

Aqueous organic peroxide emulsions comprising such plasticisers were found to be more stable upon storage than known emulsions. In addition, the plasticiser can be used in relatively small amounts.

The present invention relates to aqueous organic peroxide emulsions comprising an organic peroxide which is a liquid at storage and handling temperatures. Hence, other types of organic peroxide dispersions such as suspensions are excluded from the claims of this patent application. Typically, the aqueous organic peroxide emulsions in accordance with the present invention are fluids. As the skilled man will know, emulsions are defined as a mixture of two or more immiscible liquids, one being present in the other in the form of droplets.

The ratio of the number of carbon atoms present in the plasticiser molecule (excluding aromatic carbon atoms) to the number of ester groups in the molecule is represented by Ap/Po. Preferably, the Ap/Po ratio is 9 to 40, more preferably, 9 to 30, even more preferably, 9 to 20, and most preferably, 10 to 15.

The Ap/Po ratio is a generally accepted expression to characterise ester plasticisers. See A. S. Wilson, *Plasticisers: Principles and Practice,* The Institute of Materials, Cambridge University Press, 1996, p. 12.

The plasticisers to be used in the emulsions according to the present invention, i.e. esters having an Ap/Po ratio higher than 8 are known compounds. See A. S. Wilson, *Plasticisers: Principles and Practice,* The Institute of Materials, Cambridge University Press, 1996, pp. 145–179 (Chapter 5) and 279–280 (Appendix 1). A person of ordinary skill in the art of application of the emulsions in accordance with the present invention, in particular their use in the manufacture of PVC, will have no difficulty in selecting a suitable plasticiser for use in accordance with the present invention.

Suitable ester plasticisers include phthalates, terephthalates, benzoates, adipates, citrates, sebacates, trimellitates, sulphonates, phosphates, fatty acid esters, and mixtures thereof. Preferably, the ester plasticiser is selected from the group consisting of phthalates and adipates and mixtures thereof.

More specific examples of ester plasticisers useful in the emulsions of the present invention are dinonyl phthalate, diisononyl phthalate, didecyl phthalate, diisodecyl phthalate, diundecyl phthalate, diisoundecyl phthalate, didodecyl phthalate, ditridecyl phthalate, diisotridecyl phthalate, ditetradecyl phthalate, dipentadecyl phthalate, dihexadecyl phthalate, dioctadecyl phthalate, dinonyl adipate, didecyl adipate, diisodecyl adipate, didodecyl adipate, ditetradecyl adipate, dipentadecyl adipate, dihexadecyl adipate, dioctadecyl adipate, propyl decanoate, propyl laurate, isopropyl laurate, propyl myristate, propyl palmitate, propyl stearate, butyl decanoate, butyl laurate, butyl myristate, butyl palmitate, butyl stearate, and mixtures thereof.

Preferably, the ester plasticiser used in the emulsions according to the present invention is selected from the group consisting of diisononyl phthalate, diisodecyl phthalate, diisoundecyl phthalate, diisododecyl phthalate, diisodecyl adipate, and mixtures thereof. Most preferably, the plasticiser is diisodecyl phthalate or diisodecyl adipate.

In the context of the present invention, when we speak of emulsions which are stabilised against droplet growth, what is meant is that 99 percentile of the droplet volume distribution (d99) of the organic peroxide in the emulsion does not exceed 15, preferably 10, more preferably 8, most preferably 6 μm during 12 weeks of storage at −20° C. Changes in droplet volume distribution influence the viscosity and storage stability of the emulsion, while also the polymerisation process can be adversely influenced when an emulsion with larger organic peroxide droplets is used, e.g., by having an increased number of fish eyes in the case of the production of PVC. The droplet volume distribution is determined in a conventional way by means of a light scattering technique, measured, for example, by using a Malvern type 2600 apparatus.

The amount of plasticiser required to optimise the storage stability of the aqueous organic peroxide emulsion according to this invention will depend on the type and amount of organic peroxide and the type of plasticiser used in the emulsion. Typically, an amount of 0.1 to 10, preferably 0.5 to 5, more preferably, 0.5 to 3, most preferably 0.5 to 2 wt %, based on the total weight of the emulsion, is used.

The organic peroxides that can be formulated in accordance with the present invention are liquid organic peroxides, in particular, the more polar liquid organic peroxides. The group of liquid organic peroxides includes hydroperoxides, peroxyesters, peroxycarbonates, peroxydicarbonates, diacyl peroxides, dialkyl peroxides, and bis(acylperoxy)alkanes. Preferred are peroxyesters and peroxycarbonates.

Examples of preferred organic peroxides for use in accordance with the present invention are diisobutyryl peroxide, cumyl peroxyneodecanoate, 1,1,3,3-tetramethylbutyl peroxyneodecanoate, tert-amyl peroxyneodecanoate, tert-butyl peroxyneodecanoate, dibutyl peroxydicarbonate, 1,1,3,3-tetramethylbutyl peroxy-2-ethylhexanoate, 1,1,3,3-tetramethylbutyl peroxypivalate, tert-butyl peroxyneoheptanoate, tert-amyl peroxy-2-ethylhexanoate, tert-amyl peroxypivalate, tert-butyl peroxy-2-ethylhexanoate, tert-butyl peroxypivalate, tert-butyl peroxydiethylacetate, tert-butyl peroxyisobutyrate, di(2-ethylhexyl) peroxydicarbonate, di(3,5,5-trimethylhexanoyl) peroxide, 2,5-dimethyl-2,5-di(2-ethylhexanoylperoxy)hexane, 1-hydroperoxy-1,3-dimethylbutyl peroxypivalate, 1-(2-ethylhexylperoxy)-1,3-dimethylbutyl peroxypivalate, 2-(2-ethylhexanoylperoxy)-2-(pivaloylperoxy)-4-methyl-pentane, and 2-(2-ethylhexyloxycarbonylperoxy)-2-(isobutanoylperoxy)-5-methyl-hexane.

More preferably, the organic peroxide to be used in accordance with the present invention is selected from the group consisting of cumyl peroxyneodecanoate, tert-butyl peroxyneodecanoate, diisobutyryl peroxide, 1,1,3,3-tetramethylbutyl peroxyneodecanoate, tert-amyl peroxyneodecanoate, di(2-ethylhexyl) peroxydicarbonate, di-sec-butyl peroxydicarbonate, tert-butyl peroxyneoheptanoate, tert-amyl peroxypivalate, tert-butyl peroxypivalate, di(3,5,5-trimethylhexanoyl) peroxide, 1-(2-ethylhexylperoxy)-1,3-dimethylbutyl peroxypivalate, and (2-(2-ethylhexanoylperoxy)-2-(pivaloylperoxy)-4-methylpentane. Most preferably, the organic peroxide to be used in accordance with the present invention is selected from the group consisting of cumyl peroxyneodecanoate, tert-butyl peroxyneodecanoate, tert-butyl peroxyneoheptanoate, and 1-(2-ethylhexylperoxy)-1,3-dimethylbutyl peroxypivalate.

The aqueous organic peroxide emulsions in accordance with the present invention typically contain 30–70 wt % of organic peroxide, based on the total weight of the emulsion. Preferably, the amount of organic peroxide in the emulsion is 35–65, more preferably 40–60, most preferably 50–60 wt %.

Any conventional anti-freeze agent can be used—in a usual amount—in the aqueous emulsions according to the present invention. Preferably, use is made of methanol, ethanol, isopropanol, (ethylene) glycol, propanediol, glycerol, and mixtures thereof, more preferably, methanol, ethanol, and mixtures thereof. These agents are known to have hardly any effect on polymerisation processes. A skilled person will have no difficulties in balancing the ratio of water to anti-freeze agent(s). Typically, the amount of anti-freeze agent used in the emulsion according to the present invention will be lower than the amount of water, as shown in the Examples given below.

Any conventional protective colloid can be used in the aqueous emulsions according to the present invention. Suitable protective colloids include partially hydrolysed (or saponified) polyvinyl acetates, polyvinyl pyrrolidones, polyacrylates, cellulose, cellulose derivatives, starch, and starch derivatives. Particularly useful are partially hydrolysed/saponified polyvinyl acetates, cellulose, cellulose derivatives, starch, and starch derivatives. Typically, a polyvinyl acetate (PVA), preferably having a degree of hydrolysis of 50–75 mole %, is used.

The amount of protective colloid used in the emulsions according to the present invention will depend on the type and amount of organic peroxide and the desired viscosity of the final emulsion. Typically, the amount of protective colloid in the final emulsion will be between 0.5 and 10, preferably between 0.5 and 5, more preferably between 0.5 and 3, most preferably between 0.5 and 2 wt %, based on the total weight of the emulsion.

Preferably, the emulsion in accordance with the present invention further contains a conventional emulsifier. Suitable emulsifiers are known to the person skilled in this art and they include non-ionic, anionic, cationic, and amphoteric surfactants, and mixtures thereof. They may be incorporated in their usual amounts. Preferably, a non-ionic surfactant, more preferably having an HLB (hydrophile-lipophile balance) value of 7 or higher, even more preferably 16 or higher, is used.

The aqueous organic peroxide emulsions of the present invention optionally may also contain other additives including pH-adjusting agents such as phosphate and citrate buffers, sequestering agents, biocides, e.g. fungicides, antiozonants, antioxidants, antidegradants, U.V. stabilisers, coagents, comonomers, antistatic agents, blowing agents, mould release agents, and process oils. These additives may be added in their usual amounts.

The emulsions of the present invention can be produced in a conventional manner. Typically, the ingredients of the emulsion are mixed and/or homogenised using well-known equipment, such as high-speed mixers, colloid mills, pearl mills, ball mills, pressure homogenisers, fluidisers, and ultrasonic homogenisers. Because many of the organic peroxides which are used in accordance with the present invention are not stable at higher temperatures, the mixing and/or homogenising typically is carried out below a temperature of 15° C., preferably, well below the self-accelerating decomposition temperature (SADT) of the organic peroxide.

The present invention also relates to the use of the above-described aqueous organic peroxide emulsions in polymerisation processes, cross-linking reactions, the curing of unsaturated polyester resins, polymer modification processes, and other reactions involving free radicals, like the synthesis of certain chemicals.

The emulsions of the present invention preferably are used in polymerisation processes, more preferably, the polymerisation of vinyl chloride monomer (VCM) and copolymerisation of VCM with styrene or (meth)acrylate. Most preferred is the use of the emulsion in accordance with the present invention in a suspension polymerisation process for preparing PVC.

The present invention is further illustrated by the following Examples.

EXAMPLES

Materials

PVA: Polyvinyl acetate, degree of hydrolysis 62.5–67.5%, ex Unitika

Trigonox® 99: Cumyl peroxyneodecanoate, ex Akzo Nobel, different grades were used as indicated in the Examples below.

Trigonox® 23: Tert-butyl peroxyneodecanoate, ex Akzo Nobel

Ketjenlube® 16: Diisodecyl adipate (DIDA), ex Akzo Nobel

Jayflex: Diisodecyl phthalate (DIDP), ex Exxon

Vestinol N: Dinonyl phthalate (DNP), ex Hüls

Dioctyl phthalate: Di-2-ethylhexyl phthalate (DOP), ex Acros

General Procedures

In the following Examples, the aqueous organic peroxide emulsions were made by the following general procedure: to a cooled vessel at −10° C. were added in succession organic peroxide (final content is 50 wt %, based on the total weight of the emulsion), PVA (see Tables), plasticiser ester (see Tables), the remainder being a mixture of water/methanol in the ratio indicated in the Examples below. The organic peroxide was dispersed using an UltraTurrax type S25N-25GM (4 minutes/kg of emulsion) at full power, during which the temperature of the emulsion was kept below 15° C.

The droplet volume distribution was determined by means of a light scattering technique, using a Malvern type 2600 apparatus. In the Tables, d99 (expressed in μm) is 99 percentile of the droplet volume distribution of the organic peroxide in the emulsion (reproducibility approx. 0.5 μm). The emulsion samples were stored at −20° C. and the data were collected at room temperature.

All other numbers are expressed as wt %, based on the total weight of the emulsion.

Example 1 and Comparative Examples A and B

Organic peroxide: cumyl peroxyneodecanoate, 80%.
Protective colloid: PVA, degree of hydrolysis 62.5–67.5%
Water/methanol=72/28

TABLE 1

| | Example | | |
|---|---|---|---|
| | 1 | A | B |
| PVA | 1.5 | 1.5 | 1.5 |
| DIDA | 1.0 | — | — |
| DOP | — | — | 1.0 |

TABLE 1-continued

| | Example | | |
|---|---|---|---|
| | 1 | A | B |
| d99 (μm) | | | |
| After 1 day | 2.2 | 2.5 | 2.1 |
| After 12 weeks | 3.7 | 7.1 (8 weeks) | 6.5 |

These data show that DOP (Ap/Po=8) inhibits the growth of droplets to some extent, but that DIDA (Ap/Po=12) is far superior to DOP.

Examples 2 and 3 and Comparative Example C

Organic peroxide: cumyl peroxyneodecanoate, 77%.
Protective colloid: PVA, degree of hydrolysis 62.5–67.5%
Water/methanol=75/25

TABLE 2

| | Example | | |
|---|---|---|---|
| | 2 | 3 | C |
| PVA | 1.0 | 1.0 | 1.0 |
| DIDP | 1.0 | — | — |
| DNP | — | 1.0 | — |
| DOP | — | — | 1.0 |
| d99 (μm) | | | |
| After 1 day | 3.7 | 3.9 | 3.9 |
| After 12 weeks | 5.9 | 7.1 | 8.7 |
| After 16 weeks | 5.2 | 8.5 | 10.1 |

These data illustrate that DIDP (Ap/Po=10) and DNP (Ap/Po=9) inhibit the growth of droplets in the emulsion more effectively than DOP.

Examples 4 and 5 and Comparative Example D

Organic peroxide: tert-butyl peroxyneodecanoate, 98%.
Protective colloid: PVA, degree of hydrolysis 62.5–67.5%
Water/methanol=70/30

TABLE 3

| | Example | | |
|---|---|---|---|
| | 4 | D | 5 |
| PVA | 2.0 | 2.0 | 2.0 |
| DIDA | 1.0 | — | — |
| DOP | — | 1.0 | — |
| DNP | — | — | 1.0 |
| d99 (μm) | | | |
| After 1 day | 3.4 | 3.5 | 3.4 |
| After 12 weeks | 4.0 | 6.1 | 4.4 |
| After 16 weeks | 3.9 | 7.4 | 5.0 |

These data illustrate the superiority of DIDA and DNP over DOP with respect to droplet growth inhibition.

The invention claimed is:

1. An aqueous organic peroxide emulsion comprising an organic peroxide that is liquid at storage and handling temperatures, an anti-freeze agent, a protective colloid, and 0.5 to 3 wt % of a plasticiser based on a total weight of the emulsion, wherein the plasticiser is an ester having a ratio of the number of carbon atoms present in the plasticiser molecule (excluding aromatic carbon atoms) to the number of ester groups in the molecule of higher than 8.

2. The emulsion according to claim 1, wherein the ratio defined in claim 1 for the ester plasticiser is 9 to 40.

3. The emulsion according to claim 1, wherein the ester plasticiser is selected from the group consisting of phthalates and adipates.

4. The emulsion according to claim 1, wherein the ester plasticiser is selected from the group consisting of diisononyl phthalate, diisodecyl phthalate, diisoundecyl phthalate, diisododecyl phthalate, diisodecyl adipate, and mixtures thereof.

5. The emulsion according to claim 1, wherein the antifreeze agent is selected from the group consisting of methanol, ethanol, isopropanol, (ethylene) glycol, propanediol, glycerol, and mixtures thereof.

6. The emulsion according to claim 1, wherein the protective colloid is a partially hydrolysed polyvinyl acetate.

7. The emulsion according to claim 1, wherein the emulsion contains an emulsifier.

8. The emulsion according to claim 7, wherein the emulsifier is a non-ionic surfactant.

9. A method for polymerizing vinyl chloride monomer, comprising polymerizing vinyl chloride monomer in the prescence of the emulsion according to claim 1.

* * * * *